United States Patent [19]

Krupey

[11] Patent Number: 5,019,521

[45] Date of Patent: May 28, 1991

[54] PAIRED POLYPEPTIDES

[75] Inventor: John Krupey, Glen Rock, N.J.

[73] Assignee: Photest Diagnostics, Inc., Waldwick, N.J.

[21] Appl. No.: 491,523

[22] Filed: Mar. 12, 1990

[51] Int. Cl.$^5$ .................. G01N 33/53; G01N 33/544; C12Q 1/00; C12N 11/06

[52] U.S. Cl. .................................. 436/500; 435/968; 435/181; 436/529; 436/540; 436/800; 436/536; 422/61

[58] Field of Search .................. 436/500, 7, 518, 536, 436/540, 537, 506, 519

[56] References Cited

U.S. PATENT DOCUMENTS 4,891,313 1/1990 Berger et al. .................. 436/518

Primary Examiner—Robert A. Wax
Assistant Examiner—Bradley L. Sisson
Attorney, Agent, or Firm—Ralph T. Lilore

[57] ABSTRACT

Binding assay reagents for use in optical assay systems are disclosed. Assays, such as immunoassays, employing the reagent are also disclosed. The reagent is comprised of paired, associated polypeptides one of which has multiple optically active dye labels. The binding assay reagents exhibit enhanced binding activity over that of the dye labelled polypeptides alone and also enhance the sensitivity of the binding assay by providing increased amounts of optical label.

15 Claims, No Drawings

PAIRED POLYPEPTIDES

SUMMARY OF THE INVENTION

A reagent for optical assays has been developed which provides both increased amounts of optical label for sensitivity and enhanced levels of binding to target molecules. The agent consists of a pair of associated polypeptides, i.e. a first polypeptide with molecular mass $\geq 2$ and preferably $\geq 3.8 \times 10^5$ Daltons and most preferably $5-10 \times 10^5$ Daltons, and a second polypeptide with molecular mass approximately $2 \times 10^4$ to $2 \times 10^5$ Daltons. The larger polypeptide ("backbone") carries the optical label and a binding molecule such as antibody, antigen, avidin or biotin to form a "dye polymer conjugate". The second polypeptide ("enhancing peptide") is complexed with the dye polymer conjugate and enhances binding of these molecules and accelerates the specific binding of the conjugate with the ligand in a subsequent immunoassay. The resulting reagent may be used as an optical reagent in assay systems involving specific binding of a binding molecule with its target molecule The backbone polypeptides employed in the preparation of the dye polymers contain lysine and glutamic acid in molar proportions such that the polypeptide has a net positive charge. Preferably, lysine and glutamic acid are present in the polypeptide in an approximate molar ratio of 3-5:1 most preferably 4:1, respectively The free amino groups of the polypeptide backbone are labelled with an optical dye to form a dye polymer. Optically active dyes such as fluorescein, rhodamine, or any other optically active dye known in the art which can be coupled to a polypeptide may be used to label the polypeptide backbone, which itself is covalently linked to a binding molecule such as antibody, antigen, avidin or biotin to form a dye polymer conjugate.

The polypeptide backbone of the present invention is capable of being highly substituted with the dye, thus providing improved sensitivity to the assay system. For example, substitution with fluorescein results in binding of optical label to approximately 60-70% of the peptide's free amino groups. The remaining amino groups are available for covalent coupling of the binding molecule. It would be very desirable to use this dye polymer as a reagent for assay systems because of the large amount of label molecules it provides. Unfortunately, for various reasons not fully understood, the binding molecule portion of the dye polymer does not bind to target molecules very well, if at all. It was therefore surprising to discover that the provision of an enhancing peptide in admixture or complexed with the dye polymer conjugate enhances the binding parameter of the dye polymer in such a way as to make a relatively useless reagent eminently suitable for immunoassays.

The enhancing peptide is composed of a mixture of basic and acidic amino acid residues, and may have equal numbers of positive and negative charges, or a net negative charge. Preferably, the basic and acidic amino acids have opposite stereochemical configurations (i.e., D and L amino acids). Alternatively, the enhancing peptide may be formed of a mixture of homopolymers of a basic amino acid and homopolymers of an acidic amino acid. It is believed that the enhancing peptides, because of their combined stereo chemical arrangement, bind to the dye polymer conjugate to form an assay reagent complex which exhibits significantly enhanced binding qualities in assay procedures when compared to the dye polymer conjugate used alone. Preferably, the molar ratio of acidic amino acid residue to the basic amino acid residue is in the range of 2:1 to 1:1 and most preferably about 1:1. The reagent of the present invention is a mixture (probably a complex) of the dye polymer conjugate with the enhancing peptide in concentrations which vary depending upon the molar ratio of acidic residue to basic residue in the enhancing peptide. For example, as the ratio of acidic residue increases, the amount of enhancing peptide required to achieve the same result obtained with the lower ratio increases. Thus, suitable concentrations are 50% to 97% of enhancing peptide based on the total weight of the mixture and preferably 65% to 90% with the remaining being the dye polymer conjugate. These concentrations are based on one mg of dye polymer having 80 absorbance units.

Accordingly, it is an object of this invention to provide an optically labelled polypeptide reagent for binding assays which exhibits a high level of labelling and provides increased sensitivity in the assay.

Another object of this invention is to provide an enhancing peptide reagent for binding assays which neutralizes poor binding qualities of the labelled polypeptide reagent and enhances assay specificity and sensitivity.

Another object of this invention is to provide a paired polypeptide reagent system for use in binding assays which is composed of a complex of a labelled polypeptide (dye polymer conjugate) and an enhancing peptide.

Another object of this invention is to provide binding assays with enhanced sensitivity, improved specificity, and fast reaction rates which utilize a paired polypeptide reagent system.

Still another object of this invention is to provide methods for detecting a target molecule in a sample using a binding assay based on a paired polypeptide reagent system.

Additional objects, advantages and novel features of the invention will be set forth in part in the description which follows, and in part will become apparent upon examination of the following specification or may be learned by practice of this invention.

To achieve the foregoing and other objects in accordance with the present invention as embodied and broadly described herein, the backbone polypeptides may be synthesized according to any of the methods of peptide synthesis known to those skilled in the art. See for example, Blout, E. R. and Karlson, R. H., Journal of the American Chemical Society, 78, 941-946, March, 1956; Hanby, W. E., Waley, S. G., and Watson, J., Journal of the Chemical Society, Article 632, 3239-3249, 1950; Bodanszky, M. Bodanszky, A., The Practice of Peptide Synthesis, Springer-Varlay, Berlin, Heidelberg, New York, Tokyo, 1984, page 211; Bodanszky, M., Bodanszky, A., Principles of Peptide Synthesis, Springer Verlay, Berlin, Heidelberg, New York, Tokyo, 1984. Preferably, they are synthesized using a modified ring opening polymerization procedure utilizing amino acid N-carboxy anhydrides (Leuchs, H.: Beridtsch Chem. Ges. 39 857 (1906)1; Leuchs, H., Geiger, W., ibid 41, 1721 (1908). In this method, the cyclic mixed anhydrides of carbonic acid are prepared by reacting phosphorous pentachloride with N-a-N-e-di-CBZ-L-lysine and N-CBZ-L-glutamic acid-gamma-benzyl ester (NCA derivatives). The aprotic base sodium methoxide is used to initiate the polymerization.

Because the N-carboxyanhydride derivative of glutamic acid polymerizes at approximately three times the rate of the N-carboxyanhydride derivative of lysine, the sequence of the resulting backbone polypeptide is not completely random. One end of the final copolymer consists predominantly of glutamic acid and the other end consists predominantly of lysine. There is an excess molar ratio of lysine to glutamic acid in the polypeptide, preferably a ratio of approximately 4:1 respectively.

Dye molecules may be linked to the amino groups of the backbone polypeptide using any of the procedures known to those skilled in the art for labelling proteins and polypeptides with optical dyes such as rhodamine or fluorescein. Preferably, the backbone polypeptide of the present invention is labelled with fluorescein according to the method cited of Wier, D. M., Immunochemistry, Chapter 28, pages 405, 4th edition, Blackwell Publications, Boston, 1986, by slow addition of fluorescein isothiocyanate with subsequent purification by dialysis and molecular sieve chromatography.

After preparation of the dye polymer, the appropriate binding molecule is covalently linked to the dye polymer to form a dye polymer conjugate. Suitable methods for covalently linking binding molecules to the amino groups of polypeptides are well known in the art. See for example, Carlsson, J., Drevin, H., and Axen, R., Biochemical Journal 173, 723, 1978. Preferably, the linking method employed is a modification of that taught by Carlsson Supra, in which the polypeptide and the binding molecule are first modified with N-succinimidyl 3-(2 pyridyldithio) propionate (SPDP) and subsequently coupled through a disulfide linkage.

The enhancing peptides may also be synthesized according to any suitable procedure known in the art for synthesis of polypeptides. Preferably, they will also be synthesized using a ring opening polymerization of amino acid N-carboxyanhydrides similar to that employed for the synthesis of backbone polypeptides. Preferably, the enhancing peptides are composed of a mixture of basic and acidic amino acid residues having opposite stereochemical configurations. Most preferably, the enhancing peptide is composed of L-glutamic acid and D-lysine or D-glutamic acid and L-lysine in an approximate molar ratio of 1:1 to 2:1. While higher ratios will produce suitable results, it has been discovered that as the molar ratio of glutamic acid to lysine increases, the activity of the resulting enhancing peptide decreases thus requiring more total enhancing peptides to achieve the same desired result as those with lower molar ratios.

In an alternative embodiment, the enhancing peptide may be composed of a mixture of homopolymers of a basic amino acid and homopolymers of an acidic amino acid. In the case of mixtures of homopolymers, opposite stereochemical configuration of the basic and acidic amino acid polypeptides is not required for enhancing activity. Preferably, the homopolymers in the mixture are D-lysine (Mr 13K) with L-glutamic acid (Mr 77K) homopolymer, D-lysine (Mr 13K) with D-glutamic acid (Mr 66K) homopolymer, or D-lysine (Mr 26.3K) with D-glutamic acid (Mr 66K) wherein the amino acids are present in the same ratios as discussed above.

The paired polypeptide reagent, which is a complex of dye polymer conjugate and enhancing peptide, is useful for optical detection of the presence or absence and/or the amount of target molecules in a variety of binding assays in biological liquids such as blood, serum, plasma, urine, saliva, tears, perspiration, lymph and the like. Examples of such assays include, but are not limited to, immunoassays based on binding between antigens and antibodies or binding assays involving avidin/biotin detection systems. In such assays, the enhancing peptide significantly increases assay sensitivity and binding characteristics of the dye polymer conjugate.

In general, the inventive assay test systems employing the novel paired polypeptide reagent comprise a dye polmer conjugate carrying the appropriate binding molecule which can bind with the target molecule suspected in the assay sample, an enhancing peptide which is complexed with the dye polymer conjugate, and means for detecting and/or quantitating the optical emissions from the dye. Preferably, the assay is a competitive binding assay in which the binding molecule is bound to a solid phase to facilitate separation of the target molecule binding molecule complexes from the solution after exposure to the sample to be tested. The assay may also be a sandwich type assay in which a solid phase having immobilized on it a binding molecule directed against a portion of the target molecule is exposed to a sample containing the target molecule followed by a solution consisting of the dye polymer conjugate (complexed with enhancing peptide) containing a binding molecule directed against a different site on the same target molecule. One example of a suitable solid phase is agarose gel. Other examples of suitable solid phases will be apparent to those skilled in the art and are well known in the art of binding assays.

DETAILED DESCRIPTION OF THE INVENTION

An essential component of the paired polypeptide assay reagent and the inventive assay systems is a dye polymer conjugate consisting of a polypeptide backbone, optical dye molecules linked to the backbone through its amino groups, and a binding molecule also linked to the backbone through its amino groups. The backbone component of the dye polymer conjugate is a polypeptide with a net positive charge consisting of lysine and glutamic acid residues. Most preferably lysine and glutamic acid will be in an approximate molar ratio of 4:1 in the backbone polypeptide and most preferably it will have a molecular mass of $\geq 5\text{-}10 \times 10^5$ Daltons with $1 \times 10^6$ being usually selected and the lysine and glutamic acid will be in the L-form. Used in an immunoassay without the enhancing peptides of the present invention, they do not offer suitable binding characteristics.

The polypeptide backbone is preferably synthesized according to a modification of the ring opening polymerization method of Leuchs Supra; however, many suitable alternative methods of polypeptide synthesis will be apparent to those skilled in the art. In the ring opening polymerization method, N-carboxyanhydrides of the desired amino acids are first prepared from gamma benzyl-N-carbobenzoxy glutamate and sodium N-e, a di-carbobenzoxylysine by reaction with phosphorous pentachloride. The crystalline reaction products are purified and washed.

Sodium methoxide in optimal amounts is used to initiate the polymerization of the N-carboxy anhydride amino acids in the preparation of the enhancing peptide.

Random copolymers of the N-carboxy anhydride (NCA) derivatives of glutamic acid and lysine are synthesized by dissolving the NCA amino acid crystals in dioxane adding a sufficient amount of sodium methoxide to provide an optimal NCA amino acid:initiator ratio, reacting the mixture and evaporating the solvent. In the preparation of the polypeptide backbone the NCA amino acid:initiator ratio is approximately 500:1.

After polymerization, the protected epsilon amino and gamma carboxyl residues of lysine and glutamic acid, respectively, are deblocked using redistilled glacial acetic acid and hydrogen bromide in acetic acid. After three days at 4°-12° C., the polymer is precipitated with ether and recovered as a cake by filtering. The cake is resuspended in 0.5 M NaOH, pH is adjusted to 9-10, and the solution is dialyzed against deionized water for several days in Spectra-por membranes (from Spectrum Medical Industries, Los Angeles, California) with a 0 molecular weight cut off of approximately 8 000-10 000. After dialysis, the product is lyophilized and labelled with an optical dye such as fluorescein or rhodamine.

The optical dye label is bound to the backbone polypeptide using standard isothyocyanate reactions.

The polypeptide backbone can be highly substituted with dye and this is the characteristic that makes it such a useful material for immunoassays. For example, when substituted with fluorescein, each molecule of polypeptide backbone may contain as much as 600 or more fluorescein residues, with a molar extinction coefficient of $Em = 6 \times 10^7$ yielding a relative molecular mass of $8 \times 10^5$ Daltons. Absorbance is equal to molar absorptivity times concentration in moles per liter, i.e.

$$Em = \frac{Absorbance}{concentration\ in\ moles\ per\ liter}$$

The dye polymer is soluble in neutral or mildly alkaline aqueous media. It is also soluble in dimethylformamide. Solutions of the dye polymer are less viscous than solutions containing a similar concentration of unreacted polypeptide backbone.

Linkage of the binding molecule to the dye polymer conjugate is preferably based on the method of Carlsson Supra; however, many other suitable methods of linking binding molecules to polypeptides are well known in the art and may also be employed. According to the teaching of Carlsson the binding molecule is added to the dye labelled polymer by first modifying the dye polymer with N-succinimidyl 3-(2 pyridyldithio) propionate (SPDP). SPDP is a hetero bifunctional reagent which contains one N-hydroxy succinimide ester moiety and one s-pyridyl disulfide moiety. The ester reacts with the primary amino groups of the polymer to form stable amide bonds. Th modified polypeptide contains a 2-pyridyl disulfide structure which is reduced with dithiothreitol (DTT). The reduction reaction results in the release of pyridine thione and produces a modified polymer carrying free sulfhydryl groups (thiolated polymer). The concentration of pyridine thione released is monitored spectrophotometrically and the value obtained is a measure of the number of sulfhydryl groups introduced into the modified polypeptide.

Secondly, the binding molecule is modified with SPDP by the same methods employed to modify the dye polymer, without reduction of the 2-pyridyl disulfide structure.

SPDP modified binding molecule is covalently coupled to the thiolated polymer by mixing the two components overnight in buffer. The reaction is stopped by addition of iodoacetic acid sodium salt and the dye polymer conjugate purified by several cycles of precipitation and centrifugation The purified dye polymer conjugate is suspended in 0.15 M Tris pH 8.5 at approximately 250-400 AU/ml.

The second essential component of the paired polypeptide assay reagent and the inventive assay systems which utilize the reagent is an enhancing peptide which is a copolymer composed of residues of acidic and basic amino acids of opposite stereochemical configuration (i.e., D or L amino acids) or mixtures of homopolymers thereof in either the same or different stereochemical configuration. Examples of suitable acidic amino acids for use in the enhancing peptide are L-aspartate, D-aspartate, L-glutamic acid, and D-glutamic acid Examples of suitable basic amino acids for use in the enhancing peptide in combination with acidic amino acids of the opposite stereochemical configuration are L-lysine, D-lysine, L-arginine, D-arginine, L-histidine, D-histidine, and L-ornithine and D-ornithine.

The enhancing peptide preferably has a molecular mass of approximately $2 \times 10^4 - 2 \times 10^5$ Daltons, but values outside the range may be used. It is an important aspect of the invention that the enhancing peptide is synthesized with a ratio of acidic to basic amino acid residues which results in an equal number of positive and negative charges or an excess of negative charge. That is, the acidic component may be present in equimolar amounts or the acidic component may be in excess of the basic component to an extent to produce a maximum net negative charge of 1.5. Preferably, the enhancing peptide copolymer is composed of aspartic acid and lysine residues of opposite stereochemical configurations or glutamic acid and lysine residues of opposite stereochemical configurations and has a molecular mass of $2 \times 10^4$ to $2 \times 10^5$ Daltons. Most preferably, the enhancing peptide is a random copolymer of glutamic acid and lysine in an approximate molar ratio of 1:1, respectively, and has a molecular mass of approximately $1 \times 10^5$ Daltons.

Alternatively, the enhancing peptide may be a mixture of separate homopolymers of each of the acidic and basic amino acids. When mixtures of homopolymers are employed to reduce nonspecific binding of the dye polymer conjugate, the two homopolymers may have either the same or opposite stereochemical configuration. It has been observed, however that homopolymer mixtures in which both peptides have the L configuration are significantly less active in enhancing binding than mixtures in which D and L or two D polypeptides are mixed. Preferably, the mixtures will contain homopolymers of D-lysine (Mr=13K) and L-glutamic acid (Mr=77K) or homopolymers of D-lysine (Mr=13-26.3K) and D-glutamic acid (Mr=66K).

Although Applicants do not wish to be bound by any particular theory of the mode of action of the enhancing peptide, it is presently believed that these peptides form microcolloids or micelles that have the ability to bind to the dye polymer conjugate by virtue of their charge, shape and relatively small size. It is further believed that the resulting complex becomes more globular in shape and therefore more amenable to reaction with the target molecule It is also theorized that incorporation of D and L amino acids is important in enhancing peptide activity because the direction of the peptide chain is effectively reversed at each point where the configuration of the amino acid residue changes This is believed to result in a peptide which is more globular in shape than one which is composed of amino acids having the same configuration. It is hypothesized that a globular shape enhances binding of the enhancing peptide with the dye polymer conjugate, thus enhancing the positive effect of the enhancing peptide on the binding required in the assay systems.

In the case of mixtures of acidic and basic homopolymers, test results suggest that homopolymers with opposite charge also associate in a globular complex which is capable of efficiently binding to the dye polymer conjugate. Size of the associated complex also appears to influence binding to the dye polymer conjugate in a way which is not yet understood. For example, mixtures of D-lysine and L-glutamic acid homopolymers exhibit decreased activity when the molecular weight of at least one of the homopolymers is increased above a critical mass. This will vary upon the characteristics of the system and the various polymers and materials used.

Enhancing peptides are synthesized by a method similar to that employed in the synthesis of the polypeptide backbone previously described. N-carboxy anhydride derivatives of the appropriate acidic and basic amino acids are polymerized using sodium methoxide as the initiator of polymerization. After polymerization and deblocking of protected amino and carboxyl residues, the peptides are dialyzed against deionized water for two days in Spectra-por membranes with molecular weight cutoff of 6,000-8,000 and lyophilized.

It has been observed that the presence of aggregates of the enhancing peptide not only precipitate but inhibit complex formation with the dye polymer conjugate. Therefore, it is believed that solubility of the peptide at least partially determines the upper limit of molecular weight which is functional to reduce nonspecific binding. To assure removal of inhibitory aggregates, the lyophilized enhancing peptide is ultracentrifuged at 300,000 × g for 2 hours, and the supernatant is removed for testing to determine 1) activity in a nonspecific binding assay, 2) relative molecular mass by gel filtration, and 3) the ratio of acidic to basic amino acid residues by HPLC after acid hydrolysis.

The dye polymer conjugate and enhancing peptide are premixed for use in a subsequent binding assay with the latter being present at from 50 to 97 and preferably 65 to 90 percent by weight of the mixture of conjugate plus peptide. Although the paired polypeptide reagent of the present invention is useful for enhancing binding in nonimmunological assay such as avidin/biotin binding assays, it is particularly advantageous when used in immunological assays, especially competitive binding assays, and particularly those involving small molecules such as thyroxine ($T_4$) and large molecules such as thyroxine binding globulin (TBG), human chorionic gonadotropin (HCG) and apolisoprotein $A_1$ (apo-$A_1$).

The following examples merely illustrate specific embodiments of the invention, but it is understood that the invention is not limited thereto. All amounts of the various ingredients in the examples and elsewhere in this specification are by weight unless otherwise specified.

EXAMPLE 1

To synthesize the dye polymer conjugate, random copolymers of 4:1 L-lysine and L-glutamic acid were first synthesized using ring opening polymerization of amino acid N-carboxy anhydrides according to the following protocol.

1. Synthesis of gamma-benzyl N-carboxyl-L-glutamate anhydride (g-Bz-L-GLU NCA). All glassware was washed with soap and hot water, rinsed first with deionized water and then with acetone, and dried at 120° C. for at least 2 hours. Prior to synthesis, the reaction vessel was rinsed with the solvent to be employed in the reaction medium.

Four grams of gamma benzyl-N-carbobenzoxy L-glutamate were placed in a dry 100 ml round bottom flask equipped with a stir bar, breaking the particles of reagent to ensure dissolution. Twenty four ml dry ether were added and a drying tube inserted. The reactants were dissolved with gentle stirring at room temperature for 30 minutes. After complete dissolution, the reaction mixture was cooled to 10° C. in an ice bath while continuing stirring. Phosphorous pentachloride ($PCl_5$) powder (2.69 g) was added by rapid addition, and stirring was continued at 10° C. In about 30-40 minutes the reaction mixture solidified.

A rotary evaporator with a guard drying tube was flushed with acetone and ether. The ether phase was evaporated, leaving a white solid. Fifteen ml of dry ethyl acetate were added, swirled and evaporated. The addition of dry ethyl acetate and evaporation was repeated. A clear syrup was obtained.

The syrup was dissolved in approximately 10 ml of dry ethyl acetate. When necessary, the mixture is warmed at 50° C. in an oil bath. Dry hexane was added until the solution became cloudy. The solution was cooled to room temperature and then placed in the freezer overnight, making sure the flask was equipped with a drying tube.

The resulting crystals were filtered on a Buchner funnel, using P-4 Fisher filter paper, washed twice with hexane and dried under vacuum in a dessicator. The melting point of the product should be 84°-88° C.

2. Synthesis of N-e-CBZ-N-a-carboxy-L-lysine NCA. Five grams of N-a-N-e di-CBZ-L-lysine were placed in a dry 100 ml round bottom flask equipped with a stir bar. Twenty five ml dry ether was added and the mixture stirred to a slurry. After cooling in a 10° C. ice and water bath, 2.8 grams phosphorous pentachloride were added to the slurry while continuing stirring at 10° C. In about 30 minutes, a clear solution resulted.

Ether was removed by roto-evaporation and co-evaporation with dry ethyl acetate (two 15 ml. portions). A white solid was obtained.

The product was recrystallized from 15 ml dry ethyl acetate and approximately 5 ml of dry hexane, warming the solution to about 50° C. in an oil bath before adding the hexane. It was then cooled to room temperature and placed in a refrigerator at 4° C. overnight in a vessel with a drying tube.

The crystals were collected on a Buchner funnel, washed with hexane and dried under vacuum. Melting point of the product should be between 90°-95° C.

3. Synthesis of random copolymers 0.95 grams of g-benzyl-L-glutamic NCA was placed in a 500 ml round bottom flask with a stirring bar and a drying tube. Fifty seven ml of dry dioxane (Aldrich Sure Seal) was added and stirred to dissolve. A colorless solution resulted.

4.38 grams of N-e-CBZ-N-a-carboxy-L-lysine NCA was placed in a dry 100 ml flask and 44 ml of dioxane was added. A colorless solution resulted.

The lysine solution was added to the glutamic acid solution, followed by 0.25 ml of freshly prepared 0.14M sodium methoxide solution in anhydrous methanol to yield an anhydride:initiator ratio of 500:1. Sodium methoxide was added dropwise from a syringe while vigorously stirring the NCA solution. After addition of the initiator, a drying tube was placed on the flask. The reaction was stirred at room temperature for 1 hour, then kept overnight at room temperature protected from light.

On the next day, solvents were removed by rotary evaporation and a pasty residue was obtained The product was dried in a vacuum dessicator over Drierite for at least 4 hours.

4. Deblocking the polypeptide Fifty ml of redistilled glacial acetic acid was added to the protected polypeptide and the mixture was swirled to dissolve most of the solid particles, about 15 minutes One hundred ml of 30% hydrogen bromide in acetic acid was then added.

After stirring for 1 hour at room temperature in the absence of moisture, a clear to yellowish solution will result which will turn cloudy in about 15-20 minutes At that time, the flask was transferred to a cold box and stirred for 3 days (4°-12° C.) A thick slurry was formed.

After three days in the cold, one volume of ether (150-200 ml) was added and the mixture was kept in the freezer for 2 hours. The precipitate was filtered on a Buchner funnel equipped with P-4 filter paper and the cake was washed twice with 20 ml of ether.

The cake was transferred to a 250 ml conical flask and 100 ml of 0.05 M NaOH was added, forming a hazy solution The pH was adjusted to 9-10. Water was added to make 150 ml, and the sample was placed in Spectrapor membranes with a molecular weight cutoff of about 8,000 to 10,000 Daltons. The sample was dialyzed against 4 × 8 L volumes of deionized water for two days at room temperature, and lyophilized.

5. Characterization of the polypeptide The relative molecular mass (Mr) was determined by gel filtration on a calibrated Sepharose CL-6B column.

The lysine to glutamic acid ratio was determined by HPLC and found to be 4.00:1.01. Varying ratios can be produced by making the appropriate changes in starting materials in the above procedures.

6. Labelling the polypeptide backbone. The random copolymer of L-lysine and L-glutamic acid (the polypeptide backbone), was labelled with fluorescein by the addition of fluorescein isothiocyanate (FITC) using the following procedure:

1. Purification Of Peptide Backbone (a) 100 milligrams of a random copolymer {poly (Glu, Lys HBr) 1:4 Approx Mol wt 380,000 (purchased from Sigma Chemical Company, St. Louis, MO., Cat No. P-0650)} were dissolved in 100 milliliters of bicarbonate buffer 0.15 M pH 9.5.

The solution was dialysed against 2 × 1L volumes of the same buffer for 48 hours at room temperature.

2. Preparation of FITC Labelled Peptide Backbone (a) The retentate (containing 75 mg of peptide backbone) was placed in a 250 ml amber flask equipped with a stirring bar).

(b) 350 mg of fluorescein isothiocyanate were weighed out and dissolved in 65.0 ml of dry dimethyl formamide contained in a dry amber flask.

(c) The FITC solution was transferred to a dry amber colored separatory funnel.

(d) While vigorously stirring the peptide solution, FITC was added at a rate of approximately 1 drop per 2 seconds.

(e) After FITC addition, the reaction was allowed to proceed for 5 hours with stirring.

3. Purification of FITC Labelled Peptide Backbone (a) The FITC-labelled backbone polymer was dialyzed against 2 × 4L volumes of bicarbonate buffer for 2 days.

(b) The FITC-labelled peptide was processed through a Spectrum Ultra filtration device equipped with Spectra/Por UF Membrane (MWCO 1 × $10^6$) Spectrum Medical Industries, Los Angeles, CA and eluted with 1.0L of 0.05M sodium phosphate buffer pH 9.0, and then concentrated to a volume of 25ml.

(c) The solution was purified on Sephadex G-25 column (2.5 cm × 54 cm) previously equilibrated with 0.05 M phosphate buffer pH 7.5.

(d) The void peak fraction (50 ml) was collected.

4. Characterization of the FITC Labelled Peptide Backbone (a) The number of absorbance units of polymer contained in the void peak eluate from the Sephadex G-25 column was determined.

(b) 5.0 ml of eluate was precipitated with 10% acetic acid, the pellets washed with water, centrifuged, and then lyophilized.

(c) The weight of residue was determined and the number of absorbance units contained in 1.0 milligram of residue using (b) as the reference volume was calculated.

The FITC labelled polypeptide (dye polymer) was then conjugated to antibody using the following method.

1. SPDP derivatization of antibody and dye polymers Ethanol (6.67 ml) was placed into a glass conical centrifuge tube using an ethanol rinsed syringe. In a dry room, ethanol was added to 10 mg SPDP (kept in dessicator) to 1.5 mg/ml. In the laboratory, the components were mixed well until dissolved (10-15 minutes).

Seventy mg of antibody were placed in an amber vial. (Antibody concentration should be between 3 and 5 mg/ml.) 8.6 moles of SPDP per mole of antibody was added in four aliquots at 5 minute intervals while mixing. The vial was then removed from stirring and let stand for 75 minutes to allow reaction to occur.

10,000 AU of dye polymer at 150-200 AU/ml was measured and placed in a 100 ml amber bottle. 3.5 ml of the remaining SPDP was diluted to 10.5 ml with ethanol (final concentration 0.5 mg/ml SPDP). Thirty moles SPDP per mole of dye polymer was added in four aliquots at 5 minute intervals while stirring. Stirring was continued for an additional 2 hours and 15 minutes.

The SPDP derivatized antibody was dialyzed in 2.5 cm. dialysis tubing against 1 liter of 0.1 M P04, 0.1 M NaCl, pH7.4 buffer overnight at 4° C.

The SPDP derivatized dye polymer was dialyzed against 2 liters of 0.05 M P04, pH 7.5, overnight at 4° C.

2. Reduction of SPDP derivatized dye polymer. The dye polymer was removed from the dialysis tubing and the total volume was measured. The amount of 0.2 M DTT to be added to the dye polymer to obtain a final concentration of 0.02 M.DTT (dye polymer volume × 11%) was calculated and the dye polymer and calculated volume of DTT were reacted for one hour in a clean capped amber bottle with stirring.

After reaction, the reduced polymer was precipitated by lowering the pH of the solution to 5 with 10 percent acetic acid. Samples were transferred to 50 ml conical tubes and centrifuged in the cold. Supernatants were saved for determination of pyridine-2-thione, a measure of the number of sulfhydryl groups introduced into the polymer.

Each pellet was dispersed in 50 ml of 0.01 M acetate buffer, pH 5, mixed well and centrifuged. Supernatants were discarded and the procedure repeated. Centrifuge tubes were changed and the product washed 3 more times with 0.01 sodium acetate, centrifuging in the cold and discarding supernatants.

Pellets were washed once with deionized water, and the supernatants discarded The pellet was then dissolved in 1.0 ml of 0.05 M PO4, pH 7.4 for each 200 AU of starting material. Immediately, the pH was adjusted to 7.5 with 0.5 M dibasic sodium phosphate. A portion (0.1 ml) of the polymer was diluted 1:200 with 0.15 M Tris buffer pH 8.5 and read at 492 nonaometers. Concentration and total AU recovered were calculated. Samples were diluted to approximately 100 AU/ml in preparation for conjugation. (Once the reduced polymer has been dissolved, the antibody should be added within 30 minutes.)

The thiol group concentration was calculated according to the method of Carlsson Supra.

3. Processing of SPDP antibody SPDP Antibody was removed from the dialysis tubing and the volume measured Antibody concentration was determined by reading the absorbance at 280 nonameters.

4. Conjugation of dye polymer to antibody. The total mg of antibody available and the total AU of reduced polymer available were calculated. Using 6.6 mg of SPDP modified antibody for each 1,000AU of polymer, the amount of conjugate that could be made was calculated, reserving 1.0 mg of SPDP antibody for testing of thiol groups.

Reduced polymer was placed in a clear glass bottle with a stir bar at 100 AU/ml. Antibody was added while the mixture was stirring, then the mixture was removed from the stir plate and incubated overnight at room temperature. (The number of thiol groups on the antibody had been calculated according to the method of Carlsson.)

The conjugation reaction was stopped the following day by adding 100 1 of 1.0 M iodoacetic acid, sodium salt for each 10,000 AU. After mixing for a few minutes the mixture was let stand for two hours without stirring.

5. Purification of conjugate by precipitation. The conjugate was transferred to one 50 ml plastic centrifuge tube for each 2500 AU and the pH was lowered to 5.5 with 1.0M monobasic sodium phosphate. After centrifuging in the cold, the supernatant was discarded.

Each pellet was dispersed in 50 ml cold 0.15 M NaCl, centrifuged and decanted The washing procedure was repeated.

The pellet was redissolved in approximately 10 ml 0.01M Tris, pH 8.5, then transferred to a clean 50 ml plastic centrifuge tube. pH adjustment, centrifugation and NaCl washes were repeated. Each pellet was redissolved in 10 ml of 0.01 M Tris, pH 8.5, and the procedure repeated again with clean centrifuge tubes, finally redissolving the pellets at approximately 250 to 400 AU/ml in 0.15 Tris pH 8.5. Three 20ul aliquots were diluted to 4 ml with 0.15 M Tris (1:200) and O.D. read at 492 monochromatic. An average reading multiplied by 200 was used to obtain concentration.

EXAMPLE 2

Synthesis of a representative enhancing peptide consisting of L-glutamic acid and D-lysine in a molar ratio of 6:4, respectively, was accomplished as described in Example 1 for synthesis of the backbone polypeptide, with the following modifications.

1. The quantity of g-benzyl-L-glutamic acid NCA employed was 2.84 grams.
2. The quantity of N-e-CBZ-N-a carboxy-D-lysine NCA employed was 2.19 grams.
3. The volume of sodium methoxide employed was 2.5 ml in order to obtain an anhydride initiator ratio of 50:1.
4. The peptide obtained after dialysis was ultracentrifuged at 300,000 xg for 2 hours. The supernatant was recovered and lyophilized.
5. Characterization of the polypeptide: The relative molecular mass (Mr) was determined by gel filtration on a calibrated Sephacryl S-300 column.
6. The glutamic acid to lysine ratio was determined by HPLC and found to be 6.02 to 4.01. Ratios higher or lower than the foregoing may be made by making appropriate adjustments in the amounts of glutamic acid and/or lysine used in the foregoing procedures.

EXAMPLE 3

COMPARISON OF ACTIVITY OF ENHANCING PEPTIDES

Enhancing peptides composed of 6:4 ratios of L-glu:D-lys, D-glu:L-lys, L-asp:D-lys, L-glu:D-lys, D-glu:D-lys, and mixtures of homopolymers of D-lys and L-glu or L-lys and D-glu were tested in immunoassays for their activity in enhancing the binding of the dye polymer conjugate to the target molecule in immunological reactions.

TBG Immunoassay: The TBG immunoassay is based upon the ability of the anti-TBG-dye polymer conjugate to bind circulating TBG with subsequent capture of the anti-TBG-dye polymer-TBG complex with $T_4$ immobilized on a solid phase.

Anti-TBG-dye polymer conjugate (8AU), 100 milligrams, prepared as in Example 1 was premixed with 400 microliters of a 2.5% solution of a 6:4 D-glu:L-lys enhancing peptide in 0.05 M Tris buffer, pH 8.5 containing 2 mg. of enhancing peptide prepared as in Example 2. This mixture now containing approximately 96% of enhancing peptide (based the weight of dye polymer plus enhancing peptide) was added to the specimen containing TBG. One milliliter of gel suspension carrying immobilized $T_4$ was then added and the increase in absorbance of the liquid phase at 492 nm was determined after 60 minutes incubation. Increases in absorbance of at least 300 milli AU were considered to represent significant enhancing peptide activity.

In this immunoassay, an enhancing peptide of 6:4L-glu:D-lys gave a change in absorbance of approximately 2000 milli AU in samples containing approximately 60 micrograms of TBG per milliliter. Similar enhancing peptides composed of L-glu and L-Lys or D-glu and D-lys gave little or no change in absorbance in this assay, suggesting that enhancing peptides in which the acidic and basic amino acids have the same stereochemical configuration do not significantly enhance binding of the dye polymer conjugate in immunoassays.

Mixtures of homopolymers of basic and acidic amino acids were also testing for inhibition of nonspecific binding in the TBG assay. Prior to addition to the dye polymer conjugate, equimolar quantities of the homopolymers were mixed in water at pH 8.5. The results obtained using a sample that contained 60 micrograms of TBG per milliliter are shown in the following Table.

TABLE 1

| | | Absorbance Change (milli AU) |
|---|---|---|
| (a) | Poly L—lys (3.5K)/Poly L—glu (70K) | 374 |
| (b) | Poly D—lys (13K)/Poly L—glu (77K) | 536 |
| (c) | Poly D—lys (13K)/Poly D—glu (66K) | 502 |
| (d) | Poly L—lys (21.5K)/Poly L—glu (77K) | 256 |
| (e) | Poly L—lys (21.5K)/Poly L—glu (66K) | 92 |
| (f) | Poly D—lys (26.3K)/Poly L—glu (77K) | 96 |
| (g) | Poly D—lys (26.3K)/Poly D—glu (66K) | 551 |

Samples a, b, c, and g exhibit acceptable qualities in enhancing binding. These results also suggest that, in contrast to single enhancing peptides where a mixture of stereochemical configuration is critical to activity, when homopolymers are used in a complex of polymers, the same stereochemical configuration may be functional. There also may be some effect of size of the complex on activity.

The following table (Table 2) shows activity of the composition over the range of normally encountered TBG concentration in patients plasma.

| TBG ANTIGEN CONCENTRATION IN MICROGRAMS PER MILLILITER | CHANGE IN ABSORBANCE AT 492 NONAMETERS (MILLIABSORBANCE UNITS) |
|---|---|
| 0 | 0 |
| 10 | 352 |
| 20 | 660 |
| 30 | 1,148 |
| 40 | 1,560 |
| 50 | 1,660 |
| 60 | 1,948 |

EXAMPLE 4

$T_4$ Association Assay: This immunoassay format is based upon the addition of anti-$T_4$ dye polymer reacted with a sample containing $T_4$, followed by addition of $T_3$ immobilized on a solid support to capture unbound anti-$T_4$ dye polymer conjugate.

One hundred microliters of a 0.2% solution of 8-anilino-napthalene sulfonate (ANS) was added to samples containing $T_4$ at the levels shown in Table 3, followed by the addition of anti-$T_4$-dye polymer conjugate (8AU) which had been previously mixed with 400 microliters of a 2.5% solution in Tris pH 8.6 of enhancing peptide prepared as in Example 2. One milliliter of a 50% gel suspension containing covalently bound $T_3$ was added last, and the mixture was incubated for 15-60 minutes Absorbance at 492 nm was read and the change in absorbance determined as previously described and calculated for the sample. In samples containing approximately 1 nonagram of $T_4$, a minimal acceptable reduction in absorbance is about 300 milli AU. Table 3 below shows the immunoreactivity of the $T_4$-monoclonal antibody-dye polymer conjugate when used with the 6:4 enhancing peptide.

TABLE 3

| $T_4$ ANTIGEN CONCENTRATION MICROGRAMS PER DECILITER | CHANGE IN ABSORBANCE AT 492 NONAMETERS (MILLIABSORBANCE UNITS) |
|---|---|
| 0 | 0 |
| 2.5 | 202 |
| 5.0 | 338 |
| 10.0 | 832 |
| 15.0 | 1256 |
| 25.0 | 1658 |

When testing of serum samples was performed with the above reagents in tabletted form, the results were in agreement with those obtained with commercially available test kits.

In the $T_4$ association assay, a random copolymer consisting of 6:4 D-glu and D-lys in enhancing activity (changing in absorbance 1,363 milli AU and 1,166 milli AU after 15 min., respectively). A random copolymer of 6:4 L-asp and D-lys also displayed acceptable enhancing activity, with a change in absorbance of 414 milli AU after one hour. When 1:1 L-glu:D-Lys enhancing peptide was used in place of the 6:4 ratio material, a ten-fold decrease in the amount of enhancing peptide produced a similar and comparable change in absorbance as the 6:4 material.

EXAMPLE 5

HUMAN CHORIONIC GONADOTROPIN IMMUNOASSAY

A reagent solution containing 8AU (0.1 mg) of HCG monoclonal antibody, FITC labelled polymer conjugate prepared as in Example 1 and 2.0 milligrams of a 6:4 enhancing peptide (prepared as in Example 2) in 1.0 milliliters of 0.05M Tris buffer pH 8.5 was prepared. The solution was mixed and allowed to stand at room temperature for 30 minutes.

To a series of tubes containing 400 microliters of 0, 100 and 200 milliIU of HCG in 0.05M, Tris buffer, was added 1.0 milliliters of the above reagent solution. The tubes were then mixed for 2 hours at room temperature.

Two milliliters of a 50% gel suspension in 0.05M Tris buffer pH 8.5 containing goat anti-HCG IgG covalently linked to Ultragel by the traditional cyanogen bromide method was then added. The tubes were then mixed for 2 hours at room temperature. An aliquot of the supernatant was withdrawn, diluted with Tris buffer and the absorbance read at 492 nonameters.

TABLE

| HCG concentration in milliIU* per tube | Change in absorbance at 492 nonameters milliabsorbance units |
|---|---|
| 0 | 0 |
| 100 | 11 |
| 200 | 56 |

1.0 milliIU = 1.3 nonagrams

It is understood that the foregoing detailed description is given merely by way of illustration and what variations may be made therein without departing from the spirit of the invention.

We claim:

1. A binding assay reagent comprising a backbone polypeptide comprising glutamic acid residues and lysine residues in proportions such that the backbone polypeptide has a net positive charge, said backbone polypeptide having a molecular mass of $\geq 2.0 \times 10^5$ Daltons, an optical dye, or alternatively, an optical label covalently bound to the backbone polypeptide, a specific binding molecule covalently bound to the backbone polypeptide, and an enhancing peptide associated with the backbone polypeptide, said enhancing peptide being comprised of a mixture of (a) acidic and basic amino acid monomer residues having opposite stereochemical configurations or (b) mixtures of homopolymers of acidic amino acids and basic amino acids wherein the homopolymers may be of the same or different stereochemical configurations, and wherein said enhancing peptide is electrically neutral or has a net negative charge.

2. The binding assay reagent according to claim 1 wherein the backbone polypeptide comprises lysine and glutamic acid in a molar ratio of approximately 4:1, respectively, and has a molecular mass of approximately $\geq 3.8 \times 10^5$ Daltons.

3. The binding assay reagent according to claim 2 wherein the enhancing peptide has a molecular mass of $2 \times 10^4$ to $2 \times 10^5$ Daltons and is selected from the group consisting of polypeptides having a 1:1 to 2:1 molar ratio of L-glutamic acid to D-lysine, or of D-glutamic acid to L-lysine, or of L-aspartic acid to D-lysine.

4. The binding assay reagent according to claim 3 wherein the optical dye is fluorescein isothyocyanate and the binding molecule is selected from the group consisting of antibodies, antigens, biotin, and avidin.

5. The binding assay reagent according to claim 4 wherein the binding molecule is an antibody to TBG, antibody to $T_4$, antibody to HCG or antibody to apo $A_1$.

6. The binding assay reagent according to claim 1 wherein the enhancing peptide is a mixture of equimolar amounts of homopolymers of acidic and basic amino acids, said mixtures being selected from the group consisting of poly L-lysine and poly L-glutamic acid, poly D-lysine and poly L-glutamic acid, poly D-lysine and poly D-glutamic acid, poly-D-lysine and poly D-glutamic acid.

7. The binding assay reagent according to claim 4 wherein the backbone polypeptide has a molecular mass of approximately $5-10 \times 10^5$ Daltons.

8. The binding assay reagent of claim 7 wherein the binding molecule is an antibody to $T_4$.

9. The binding assay reagent of claim 7 wherein the binding molecule is an antibody to TBG.

10. The binding assay reagent of claim 7 wherein the binding molecule is an antibody to HCG.

11. An in vitro diagnostics method for the detection of the amount, presence or absence of a target molecule in a liquid sample which comprises contacting the binding assay reagent of claim 1 with a liquid sample for a time and under conditions sufficient for the target molecule to react with said binding assay reagent and correlating the extent to which the reaction has taking place with the amount, presence or absence of said target molecule.

12. An in vitro diagnostic method for the detection of the amount, presence or absence of a target molecule in a liquid sample which comprises contacting the binding assay reagent of claim 4 with a liquid sample for a time and under conditions sufficient for the target molecule to react with said binding assay reagent and correlating the extent to which the reaction has taken place with the amount, presence or absence of said target molecule.

13. The method of claim 12 wherein the correlating step is performed by determining the optical absorbance of the liquid phase, and determining the amount, presence or absence of target molecule in the sample by reference to a standard curve.

14. The method of claim 13 wherein the absorbance is read at a wavelength of 492 nm to 499 nm.

15. The method of claim 14 wherein the binding molecule covalently bound to the binding assay reagent is anti-$T_4$ an antibody, anti-TBG antibody, anti-HCG antibody, or anti-ApoA antibody.

* * * * *